United States Patent
Al-Herz et al.

(10) Patent No.: US 10,059,642 B1
(45) Date of Patent: *Aug. 28, 2018

(54) PROCESSES FOR HIGH SEVERITY FLUID CATALYTIC CRACKING SYSTEMS

(71) Applicant: Saudi Arabian Oil Company, Dhahran (SA)

(72) Inventors: Mansour Ali Al-Herz, Al-Ahsa (SA); Nathan D. Hould, Ann Arbor, MI (US); Ahmed Al-Asseel, Dhahran (SA); Wala A. Algozeeb, Dhahran (SA); Musaed Al-Ghrami, Dammam (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 15/967,665

(22) Filed: May 1, 2018

Related U.S. Application Data

(63) Continuation of application No. 15/190,327, filed on Jun. 23, 2016, now Pat. No. 9,981,888.

(51) Int. Cl.
*C07C 4/06* (2006.01)

(52) U.S. Cl.
CPC ............ *C07C 4/06* (2013.01); *C07C 2529/08* (2013.01); *C07C 2529/40* (2013.01); *C07C 2529/80* (2013.01)

(58) Field of Classification Search
CPC ........ B01J 27/1853; B01J 29/46; B01J 29/48; B01J 29/7676; B01J 2229/42; B01J 27/187; B01J 27/188; B01J 29/084; B01J 29/166; B01J 29/40; B01J 29/7615; B01J 29/80; B01J 35/0006; B01J 37/0045; B01J 37/031; B01J 2229/62; B01J 29/26; B01J 29/7815; C10G 11/05; C10G 11/18; C10G 2400/20

See application file for complete search history.

(56) References Cited

U.S. PATENT DOCUMENTS

| | | |
|---|---|---|
| 3,837,822 A | 9/1974 | Ward |
| 4,980,053 A | 12/1990 | Li et al. |
| 5,026,935 A | 6/1991 | Leyshon et al. |
| 5,026,936 A | 6/1991 | Leyshon et al. |
| 5,043,522 A | 8/1991 | Leyshon et al. |
| 5,160,424 A | 11/1992 | Le et al. |
| 5,171,921 A | 12/1992 | Gaffney et al. |
| 5,232,580 A | 8/1993 | Le et al. |
| 5,318,689 A | 6/1994 | Hsing et al. |
| 5,523,502 A | 6/1996 | Rubin |
| 5,549,813 A | 8/1996 | Dai et al. |
| 5,637,207 A | 6/1997 | Hsing et al. |
| 5,685,972 A | 11/1997 | Timken et al. |
| 5,770,042 A | 6/1998 | Galperin et al. |
| 5,976,356 A | 11/1999 | Drake et al. |
| 5,993,642 A | 11/1999 | Mohr et al. |
| 6,015,933 A | 1/2000 | Abrevaya et al. |
| 6,069,287 A | 5/2000 | Ladwig et al. |
| 6,210,562 B1 | 4/2001 | Xie et al. |
| 6,288,298 B1 | 9/2001 | Rodriguez et al. |
| 6,300,537 B1 | 10/2001 | Strohmaier et al. |
| 6,315,890 B1 | 11/2001 | Ladwig et al. |
| 6,455,750 B1 | 9/2002 | Steffens et al. |
| 6,521,563 B2 | 2/2003 | Strohmaier et al. |
| 6,566,293 B1 | 5/2003 | Vogt et al. |
| 6,602,403 B1 | 8/2003 | Steffens et al. |
| 6,656,345 B1 | 12/2003 | Chen et al. |
| 6,784,329 B2 | 8/2004 | O'Rear et al. |
| 6,867,341 B1 | 3/2005 | Abrevaya et al. |
| 6,979,755 B2 | 12/2005 | O'Rear et al. |
| 7,033,487 B2 | 4/2006 | O'Connor et al. |
| 7,087,155 B1 | 8/2006 | Dath et al. |
| 7,128,827 B2 | 10/2006 | Tallman et al. |
| 7,261,807 B2 | 8/2007 | Henry et al. |
| 7,270,739 B2 | 9/2007 | Chen et al. |

(Continued)

FOREIGN PATENT DOCUMENTS

WO  2010053482 A1  5/2010

OTHER PUBLICATIONS

Konno et al., "Kinetics of n-Hexane Cracking Over ZSM-5 Zeolites: Effect of Crystal Size on Effectiveness Factor an Catalyst Lifetime", Chemical Engineering Journal, 2012, 207-208: 490-496.
Konno et al., "Effectiveness of Nano-Scale ZSM-5 Zeolite and its Deactivation Mechanism on Catalytic Cracking of Representative Hydrocarbons of Naptha", Microporous and Mesoporous Materials, 2013, 175: 25-33.
Konno et al., "Characterization and Catalytic Performance of Modified Nano-Scale ZSM-5 for the Acetone-to-Olefins Reaction", Applied Catalysis A: General, 475: 127-133.
Lambert et al., "HS-FCC for Propylene: Concept to Commercial Operation", EPTQ, 2014, Q1, 39-45.
Parthasarathi et al., "HS-FCC High-Severity Fluidized atalytic Cracking: a Newcomer to the FCC Family", Appl Petrochem Res, 2014, 4: 441-444, Springer.

(Continued)

Primary Examiner — Sharon Pregler
(74) Attorney, Agent, or Firm — Dinsmore & Shohl LLP

(57) ABSTRACT

Embodiments of methods for converting gas condensate into a product stream comprising propylene comprise feeding gas condensate at a top region of a downflow high severity fluidized catalytic cracking reactor (HSFCC), where the gas condensate comprises: at least 50% by weight paraffins, and less than 0.1% by weight olefins. The method further comprises feeding catalyst to the top region of the downflow HSFCC reactor in an amount characterized by a catalyst to gas condensate weight ratio of about 5:1 to about 40:1, where the catalyst comprises nano-ZSM-5 zeolite catalyst having an average particle diameter from 0.01 to 0.2 µm, a Si/Al molar ratio from 20 to 40, and a surface area of at least 20 cm²/g. The method further comprises cracking the gas condensate in the presence of the catalyst at a reaction temperature of about 500° C. to about 700° C. to produce the product stream comprising propylene.

29 Claims, 14 Drawing Sheets

(56) References Cited

U.S. PATENT DOCUMENTS

| | | |
|---|---|---|
| 7,314,964 B2 | 1/2008 | Abrevaya et al. |
| 7,326,332 B2 | 2/2008 | Chen et al. |
| 7,374,660 B2 | 5/2008 | Steffens et al. |
| 7,459,596 B1 | 12/2008 | Abrevaya et al. |
| 7,686,942 B2 | 3/2010 | Xie et al. |
| 7,935,654 B2 | 5/2011 | Choi et al. |
| 8,137,533 B2 | 3/2012 | Towler et al. |
| 8,247,631 B2 | 8/2012 | Nicholas et al. |
| 8,652,737 B2 | 2/2014 | Handa et al. |
| 8,845,882 B2 | 9/2014 | Shu et al. |
| 8,933,286 B2 | 1/2015 | Souza et al. |
| 9,101,853 B2 | 8/2015 | Koseoglu et al. |
| 2001/0042700 A1 | 11/2001 | Swan, III et al. |
| 2001/0056217 A1 | 12/2001 | Froment et al. |
| 2002/0003103 A1 | 1/2002 | Henry et al. |
| 2003/0220530 A1 | 11/2003 | Boelt et al. |
| 2005/0070422 A1 | 3/2005 | Chen et al. |
| 2006/0108260 A1 | 5/2006 | Henry |
| 2009/0112035 A1 | 4/2009 | Choi et al. |
| 2009/0288990 A1* | 11/2009 | Xie ..................... B01J 27/1853 208/120.05 |
| 2013/0248419 A1 | 9/2013 | Abba et al. |
| 2014/0228205 A1 | 8/2014 | Narayanaswamy et al. |
| 2015/0094511 A1 | 4/2015 | Bastianti et al. |
| 2015/0152027 A1 | 6/2015 | Shafi et al. |

OTHER PUBLICATIONS

Rahimi et al., "Catalytic Cracking of Hydrocarbons over Modified ZSM-5 Zeolites to Produce Light Olefins: A Review", Applied Catalysis A: General, 2011, 398, 1-17, Elsevier.

Reding et al., Comparing Synthesis Routes to Nano-Crystalline Zeolites ZSM-5, Microporous and Mesoporous Materials, 2003, 57, 83-92, Elsevier.

Tatsumi et al., Improvement of ZSM-5 Catalysts for Cracking of Naptha:, Chemical Resources Laboratory, Tokyo Institute of Technology.

Yin et al., "One-Pot Synthesis of Hierarchically Nanoporous ZSM-5 for Catalytic Cracking", Powder Technology, 2014, 253, 10-13, Elsevier.

Zhang et al., "Nano-Crystallite Oriented Self-Assembled ZSM-5 Zeolite and its LDPE Cracking Properties: Effects of Accessibility and Strength of Acid Sites", Journal of Catalysis, 2013, 302, 115-125, Elsevier.

Tago et al., "Size-Controlled Synthesis of Nano-Zeolites and Their Application to Light Olefin Synthesis", Catal. Surv. Asia, 2012, 16, 148-163.

Mochizuki et al., "Facile Control of Crystallite Size of ZSM-5 Catalyst for Cracking of Hexane", Microporous and Mesoporous Materials, 2011, 145, 165-171.

International Serach Report and Written Opinion pertaining to Application No. PCT/US2017/038740 dated Sep. 22, 2017.

* cited by examiner

PROCESSES FOR HIGH SEVERITY FLUID CATALYTIC CRACKING SYSTEMS

CROSS REFERENCE TO RELATED APPLICATION

This application is a continuation application of U.S. patent application Ser. No. 15/190,327 filed Jun. 23, 2016, the entire disclosure of which is hereby incorporated herein by reference.

TECHNICAL FIELD

Embodiments of the present disclosure generally relate to fluid catalytic cracking processes, and more specifically relate to cracking catalysts used in high severity fluid catalytic cracking (HSFCC) systems, where the cracking catalyst comprises nano-ZSM-5 zeolites.

BACKGROUND

The worldwide increasing demand for light olefins remains a major challenge for many integrated refineries. In particular, the production of some valuable light olefins such as ethylene, propylene, and butylenes has attracted increased attention as pure olefin streams are considered the building blocks for polymer synthesis. The production of light olefins depends on several process variables like the feed type, operating conditions, and the type of catalyst. Despite the options available for producing a higher yield of propylene and light olefins, intense research activity in this field is still being conducted. These options include the use of HSFCC systems, developing more selective catalysts for the process, and enhancing the configuration of the process in favor of more advantageous setting.

The HSFCC process is capable of producing yields of propylene up to four times higher than the traditional fluid catalytic cracking unit and higher conversion levels for a range of petroleum steams. That being said, achieving maximum propylene and conversion from a wide range of feed qualities offers considerable challenges to the catalyst design for the HSFCC.

Moreover, the conventional FCC feedstocks range from hydrocracked bottoms to heavy feed fractions such as vacuum gas oil and atmospheric residue. However, these feedstocks are limited, obtained through costly and energy intensive refining steps, and thus are not expected to fulfill the ever growing market demands.

The addition of zeolites to an HSFCC catalyst is utilized for improving the yield of light olefins due to its shape selectivity, special pore structure and large specific surface area. However, when the crystal size of the zeolites is close to the molecular diameter of light hydrocarbons, the diffusion of the reactant/product molecules within the micropores is usually the rate-limiting step of the reaction. Furthermore, the crystal surface of the zeolites are susceptible to coke formation, which obstructs the accessibility of the micropores and thus deactivates the catalyst.

SUMMARY

Embodiments of the present disclosure are directed to improved HSFCC cracking systems, which convert gas condensate into light olefins using catalysts with nano-ZSM-5 catalysts, while reducing coke formation and pore diffusion on the nano-ZSM-5 zeolites.

In one embodiment, a method of converting gas condensate into a product stream comprising propylene is provided. The method comprises feeding gas condensate at a top region of a downflow high severity fluidized catalytic cracking reactor (HSFCC), where the gas condensate comprises at least 50% by weight paraffins, and, in some embodiments, less than 0.1% by weight olefins. The method further comprises feeding catalyst to the top region of the downflow HSFCC reactor in an amount characterized by a catalyst to gas condensate weight ratio of about 5:1 to about 40:1, where the catalyst comprises a nano-ZSM-5 zeolite catalyst having an average particle diameter from 0.01 to 0.2 µm, a Si/Al atomic ratio from 20 to 40, and a surface area of at least 20 $cm^2/g$. The method further comprises cracking the gas condensate in the presence of the catalyst at a reaction temperature of about 500° C. to about 700° C. to produce the product stream comprising propylene.

Additional features and advantages of the described embodiments will be set forth in the detailed description which follows, and in part will be readily apparent to those skilled in the art from that description or recognized by practicing the described embodiments, including the detailed description which follows, the claims, as well as the appended drawings.

Figure 1:
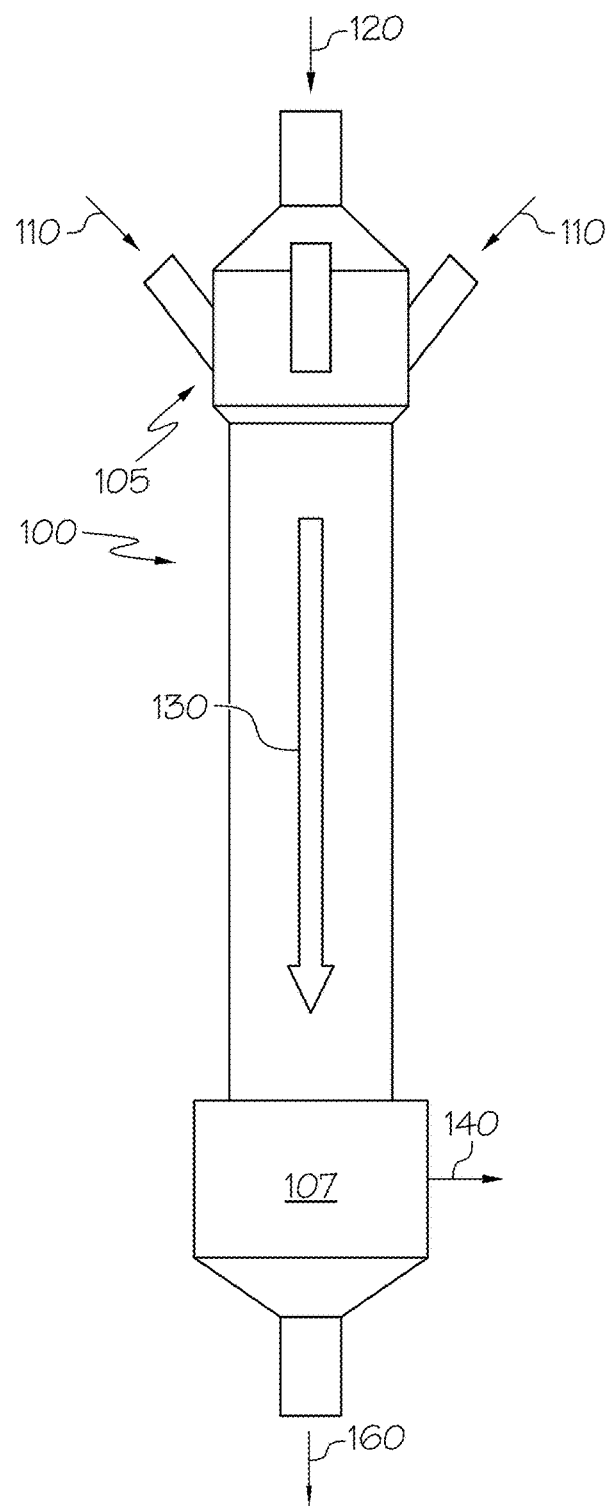
FIG. 1 is a schematic depiction of a downflow HS-FCC reactor according to one or more embodiments of the present disclosure.

The embodiments set forth in the drawings are illustrative in nature and not intended to be limiting to the claims. Moreover, individual features of the drawings will be more fully apparent and understood in view of the detailed description.

DETAILED DESCRIPTION

Embodiments of the present disclosure are directed of systems and methods of converting gas condensate into a product stream comprising propylene in a downflow high severity fluidized catalytic cracking (HSFCC) reactor in the presence of catalyst slurry comprising a nano-ZSM-5 zeolite catalyst.

Referring to FIG. 1, the system and methods utilize a downflow HSFCC reactor 100, where the gas condensate 110 may be fed at a top region 105 of the FCC reactor 100. Similarly, the catalyst 120 may be fed at the top region 105 of the HSFCC reactor 100 in an amount characterized by a catalyst 120 to gas condensate 110 weight ratio of about 5:1 to about 40:1. As shown in FIG. 1, the catalyst 120 and gas condensate 110 may be fed via different inlet ports at the top region 105 of the downflow HSFCC reactor 100. After being fed, the gas condensate 110 is cracked in the presence of the catalyst 120 at a reaction temperature of about 500° C. to about 700° C. to produce the product stream 140 comprising propylene. In some embodiments, a catalyst bed may be fixed at the bottom of the HSFCC reactor 100. While not shown, steam may be injected into the downflow HSFCC to achieve the requisite high operating temperatures. Referring to FIG. 1, the gas condensate 110 is cracked as it travels a downward path as indicated by arrow 130. As shown, the catalyst 120 and the product stream 140 may be separated through a separator region 107 at the bottom of the HSFCC reactor 100, and are then passed out of the downflow HSFCC reactor 100 separately. The gas condensate 110 and the product stream 140 comprising propylene may be separated in the separator region 107. In some embodiments, the liquid products may be collected in a liquid receiver and the gaseous products may be collected in a gas burette by water displacement.

Without being bound by theory, the present embodiments may provide a greater propylene yield in the product stream 140 as compared to conventional HSFCC reactors. In specific embodiments, the product stream 140 comprises at least a 20 wt % yield of propylene. In further embodiments, the product stream 140 may comprise at least a 10 wt % yield of ethylene. Moreover, the product stream 140 may comprise at least a 30 wt % yield of ethylene and propylene. The product stream may comprise less than a 3 wt % yield of coke, or less than 1 wt % yield of coke.

The present downflow HSFCC reactor 100 is characterized by high temperature, shorter residence times, and a high catalyst to oil ratio. In one or more embodiments, the reaction temperature is from 500° C. to 700° C., or from 550° C. to 630° C. Regarding residence time, the gas condensate may have a residence time of 0.7 seconds to 10 seconds, or from 1 second to 5 seconds, or from 1 second to 2 seconds. Moreover, the catalyst to gas condensate ratio may be from 5:1 to 40:1, or from 5:1 to 25:1, or from 5:1 to about 15:1, or from 5:1 to about 10:1.

The gas condensate 110 is a heavily paraffinic composition including at least 50% by weight paraffins and less than 0.1% by weight olefins. Additionally, the gas condensate 110 may comprise naphthenes and aromatics. From a property standpoint, the gas condensate 110 may have an initial boiling point of at least 0° C. and a final boiling point of at least 450° C. when measured according to a true boiling point analysis. The gas condensate may have a research octane number (RON) of 70 to 75 according to ASTM 2699 or ASTM 2700.

In specific embodiments, the gas condensate may comprise Khuff Gas Condensate (KGC) which comprises 65 wt % paraffins, 0 wt % olefins, 21 wt % naphthenes, and 15 wt % aromatics. Feeds like KGC have attractive feedstock properties in terms of low sulfur, nitrogen, metals and Conradson Carbon Residue (CCR). That being said, the highly paraffinic nature of gas condensate, for example, KGC, makes it quite challenging for cracking into light olefins, such as propylene. Without being limited to application, the present downflow HSFCC system overcomes these challenges and produces excellent propylene yield using KGC, while being complementary to the current refinery FCC reactors As stated previously, the catalyst 120, which may be in slurry form, comprises nano-ZSM-5 zeolites having an average particle diameter from 0.01 to 0.2 μm, a Si/Al molar ratio from 20 to 40, and a surface area of at least 20 cm$^2$/g. In further embodiments, the Si/Al molar ratio is from 25 to 35, and the nano ZSM-5 has a surface area of at least 30 cm$^2$/g. Said another way, the nano ZSM-5 has a surface area of from 30 cm$^2$/g to 60 cm$^2$/g, or from 40 cm$^2$/g to 50 cm$^2$/g. The nano-ZSM-5 zeolites solve the diffusional limitations encountered during the cracking reactions, thereby enhancing the rate of the cracking reactions to produce more olefins. Moreover, the nano-ZSM-5 zeolites reduces coke formation on the surface of the catalyst, thereby prolonging the life of the nano-ZSM-5 zeolite catalyst.

For increased catalytic cracking activity, it is contemplated that the nano-ZSM-5 zeolite catalyst may be impregnated with additional components. In one embodiment, the nano ZSM-5 catalyst is impregnated with phosphorus. In specific embodiments, the nano ZSM-5 catalyst comprises 1 to 20 wt % of phosphorus, or from 2 to 10 wt % of phosphorus. Alternatively, the nano ZSM-5 catalyst is impregnated with rare earth oxides.

Various amounts of nano-ZSM-5 zeolite are contemplated with the catalyst. For example, the catalyst may comprise from 10 to 50 wt % of nano ZSM-5 catalyst, or from 15 to 40 wt % of nano ZSM-5 catalyst, or from 15 to 25 wt % of nano ZSM-5 catalyst.

Moreover, the catalyst may also comprise USY (Ultrastable Y zeolite). For increased catalytic cracking activity, it is contemplated that the USY catalyst may also be impregnated with additional components. In specific embodiments, the USY catalyst may be impregnated with lanthanum. Various amounts of the USY catalyst are contemplated within the catalyst. For example, the catalyst may comprise 10 to 50 wt % of USY catalyst, or from 15 to 40 wt % of USY catalyst, or from 15 to 25 wt % of USY catalyst.

USY zeolite impregnation with lanthanum impacts the selectivity towards light olefins. The impregnation with rare earth can also work as an enhancer to the stability and activity of the catalyst. Lanthanum impregnation in the USY zeolite (also called Y zeolites) is used to improve both the activity and hydrothermal stability, since it acts as a dealumination inhibitor in the zeolite structure.

Various amounts of alumina are also contemplated within the catalyst. In one or more embodiments, the catalyst comprises 2 to 20 wt % of alumina, or from 5 to 15 wt % of alumina. The catalyst may also comprise silica. In one or more embodiments, the catalyst comprises 0.1 to 10 wt % of silica, or from 1 to 5 wt % of silica. Without being bound by theory, the alumina may act as a binder for the catalyst.

For example and not by way of limitation, the clay comprises one or more components selected from kaolin, montmorilonite, halloysite, and bentonite. In specific embodiments, the clay comprises kaolin. In one or more embodiments, the catalyst may comprise 30 to 70 wt % of clay, or 40 to 60 wt % of clay.

In one or more embodiments, the catalyst may comprise the nano ZSM-5 catalyst, USY catalyst, alumina, clay, and silica. In further embodiments, the catalyst comprises from 10 to 50 wt % of nano ZSM-5 catalyst, 10 to 50 wt % of USY catalyst, 2 to 20 wt % of alumina, 30 to 70 wt % of clay, and 0.1 to 10 wt % of silica. Moreover, the catalyst may comprise from 15 to 25 wt % of nano ZSM-5 catalyst, 15 to 25 wt % of USY catalyst, 5 to 15 wt % of alumina, 40 to 60 wt % of clay, and 1 to 5 wt % of silica.

EXAMPLES

The following examples illustrate one or more additional features of the present disclosure described previously.

All chemicals and solvents used in the studies are shown in Table 1.

TABLE 1

Chemicals and Solvents

| Chemical | Supplier |
|---|---|
| Ludox TM40 colloidal silica ($SiO_2$) | DuPont |
| Tetrapropylammonium hydroxide (TPAOH, $C_{12}H_{28}NOH$), 40% w/w | Alfa Aesar |
| Sodium hydroxide (NaOH) | Sigma Aldrich |
| Aluminum isopropoxide (Al(O—I—Pr)$_3$) | Sigma Aldrich |
| Y zeolite (CBV-780) | Zeolyst International |
| Formic acid | Sigma Aldrich |
| Clay | Petrobras |
| Alumina, Pural SB Grade | Petrobras |
| Diammonium hydrogen phosphate | Sigma Aldrich |
| Lanthanum Nitrate (III) hydrate | Fluka |

The main properties of Khuff Gas Condensate (KGC) utilized in the examples are shown in Table 2 as follows.

TABLE 2

| KGC Properties | |
|---|---|
| Property | Petroleum Condensate-1 |
| Density @15° C., gm/cc | 0.7695 |
| Carbon residue (MCR), wt % | 0.03 |
| Sulfur, ppm | 271 |
| Hydrogen content, wt % | 14.1 |
| Metals, ppb | |
| V | <20 |
| Ni | <20 |
| Fe | <20 |
| Na | 50 |
| PONA Analysis, wt % | |
| Paraffins | 63.9 |
| Olefins | 0 |
| Naphthenes | 21.3 |
| Aromatics | 14.8 |
| TBP analysis, wt %/° C. | |
| 5/10/30/50/80/FBP | 24/57/112/163/273/478 |

Catalyst Preparation Procedure

ZSM-5 Zeolite Synthesis

The details for the synthesis of a micron size ZSM-5 zeolites with Si-to-Al molar ratio of 100 are shown in Table 3 as follows. The details for the synthesis of nano ZSM-5 zeolites having Si-to-Al ratios of 20 and 33 are shown in Table 4 and Table 5, respectively. The precursor synthesis solutions were prepared by mixing all components and reagents together and stirring them for one day at room temperature. The mixture was then transferred into Teflon lined stainless steel autoclaves and heated to 140° C. for 4 days. After that, the solutions were centrifuged and the solid products were collected. The solid products were then dispersed in deionized water, centrifuged to obtain the final products which were then dried in the oven at 80° C. The products were calcined using the following program. Using a heating rate of 3° C./min the products were maintained at 200° C. for two hours and at 550° C. for 8 hours. The micron sized ZSM-5 were produced with a particle diameter of 1.1 μm, while the nano-ZSM-5 zeolites were produced with a particle size of 0.07 μm for a Si-to-Al molar ratio of 20 in one example, and a particle size of 0.084 μm for a Si-to-Al molar ratio of 33 in a second example.

TABLE 3

Completed synthesis solution compositions, synthesis details, yield, and phase selectivity for nano-ZSM-5 zeolites having Si-to-Al molar ratio of 100.

| | Synthesis Conditions | | | | Synthesis Sol. Composition (mole/mole) | | | | | |
|---|---|---|---|---|---|---|---|---|---|---|
| Sample | Heating Time (h) | Heating Temp. (° C.) | Synthesis Solution Mass (g) | Rotation | $H_2O$ | Ludox TM40 | NaOH | TPAOH | Al(O—I—Pr)$_3$ | Yield Product |
| SAZ-10 | 120 | 140 | 40 | static | 20 | 1 | 0 | 0.250 | 0.01 | 4.82 MFI |
| SAZ-11 | | | | | | | | | | 4.78 |
| SAZ-12 | | | | | | | | | | 4.78 |

TABLE 4

Completed synthesis solution compositions, synthesis details, yield, and phase selectivity for nano ZSM-5 zeolites having Si-to-Al molar ratio of 20.

| | Synthesis Conditions | | | | Synthesis Sol. Composition (mole/mole) | | | | | |
|---|---|---|---|---|---|---|---|---|---|---|
| Sample | Heating Time (h) | Heating Temp. (° C.) | Synthesis Solution Mass (g) | Rotation | H$_2$O | Ludox TM40 | NaOH | TPAOH | Al(O—I—Pr)$_3$ | Yield | Product |
| SAZ-25 | 120 | 140 | 40 | dynamic | 20 | 1 | 0.2 | 0 | 0.050 | 4.54 | MFI |
| SAZ-26 | | | | | | | | | | 4.53 | |
| SAZ-27 | | | | | | | | | | 4.51 | |
| SAZ-28 | | | | | | | | | | 4.31 | |

TABLE 5

Completed synthesis solution compositions, synthesis details, yield, and phase selectivity for nano ZSM-5 zeolites having Si-to-Al molar ratio of 33.

| | Synthesis Conditions | | | | Synthesis Sol. Composition (mole/mole) | | | | | |
|---|---|---|---|---|---|---|---|---|---|---|
| Sample | Heating Time (h) | Heating Temp. (° C.) | Synthesis Solution Mass (g) | Rotation | H$_2$O | Ludox TM40 | NaOH | TPAOH | Al(O—I—Pr)$_3$ | Yield | Product |
| SAZ-21 | 96 | 140 | 40 | dynamic | 20 | 1 | 0.1 | 0.250 | 0.030 | 2.14 | MFI |
| SAZ-22 | | | | | | | | | | 4.44 | |
| SAZ-23 | | | | | | | | | | 4.61 | |
| SAZ-24 | | | | | | | | | | 4.61 | |

Modification of Nano-ZSM-5 Zeolites and the Production of the Final Catalyst Formulation The following procedure was aimed at producing a catalyst formulation with the compositions reported in Table 6 as follows.

TABLE 6

Catalyst composition for in-house made HSFCC catalyst.

| Component | Weight % | Notes |
|---|---|---|
| ZSM-5 | 20 | Phosphorus impregnated at 7.5 wt % P$_2$O$_5$ on zeolite |
| USY | 21 | Lanthanum impregnated at 2.5 wt % La$_2$O$_3$ on zeolite |
| Alumina | 8 | Pural SB from Sasol |
| Clay | 49 | Kaolin |
| Silica | 2 | Added as colloidal silica Ludox TM-40 |

ZSM-5 zeolites were impregnated with phosphorous and Y zeolites were impregnated with lanthanum. The impregnated zeolites were mixed with alumina binder, silica and clay and were stirred for 1 hour. The obtained slurry was placed in temperature programmed oven for drying and calcination as per the following program: (rate (° C./min):Temperature (° C.):time (hrs))

7:125:7→3:200:1→2:320:1→2:440:7→1:500:1→7:100:1

The calcined catalyst was grounded to a fine powder by means of a mortar and a pestle. Then, the grounded catalyst was sieved for a fraction between 40-120 µm and used for characterization and evaluation.

The reactions were conducted in a Sakuragi Rikagaku (Japan) Micro Activity Test (MAT) instrument using a quartz tubular reactor. The synthesized catalysts were evaluated for cracking Khuff gas condensate according to ASTM D-3907 method. All catalysts were steamed at 750° C. for 3 h prior to the reaction. The experiments were conducted in the MAT unit at 30 s time-on-stream (TOS). After each reaction, catalysts were stripped using 30 mL/min N$_2$ flow. The liquid product was collected in the liquid receiver and the gaseous products were collected in a gas burette by water displacement and sent to the gas chromatograph (GC) for analysis. The spent catalysts were used to measure the amount of generated coke from the reaction.

The MAT results from the micro and nano-ZSM-5 based catalysts are shown in Table 7. As can be seen, high propylene yields of greater than 18 wt % were obtained for the three catalysts. The nano-ZSM-5 having Si-to-Al molar ratio of 33 achieved the highest propylene yield of 21.12 wt % compared to 20.07 wt % propylene yield obtained with the nano-ZSM-5 having Si-to-Al molar ratio of 20. The micron sized ZSM-5 achieved the lowest propylene yield of 18.78 wt % which signifies the role of the higher surface area provided by the nano ZSM-5 zeolites for the selective production of light olefins.

TABLE 7

Highlight from MAT results of in-house prepared nano-ZSM-5 based catalyst

| Catalyst | Micro-ZSM-5 (Si-to-Al = 100) | Nano-ZSM-5 (Si-to-Al = 33) | Nano-ZSM-5 (Si-to-Al = 20) |
|---|---|---|---|
| Temp. (° C.) | 650 | 650 | 650 |
| T.O.S. (s) | 30 | 30 | 30 |
| Steaming | 750 C., 3 h | 750 C., 3 h | 750, 3 h |
| Feed | KGC | KGC | KGC |
| Catalyst/KGC | 8.14 | 8.21 | 8.39 |
| Yield (mass %) | | | |
| C2= | 8.95 | 10.97 | 9.39 |
| C3= | 18.78 | 21.12 | 20.07 |
| Total Gas | 56.96 | 58.66 | 59.50 |
| Gasoline | 36.83 | 36.51 | 33.06 |
| Light Cycle Oil (LCO) | 2.01 | 2.01 | 2.78 |

TABLE 7-continued

Highlight from MAT results of in-house prepared nano-ZSM-5 based catalyst

| Catalyst | Micro-ZSM-5 (Si-to-Al = 100) | Nano-ZSM-5 (Si-to-Al = 33) | Nano-ZSM-5 (Si-to-Al = 20) |
|---|---|---|---|
| Heavy Cycle Oil (HCO) | 0.91 | 0.64 | 0.71 |
| Coke | 3.29 | 2.17 | 3.95 |
| Total | 100 | 100.00 | 100.00 |

Characterization of Nano-ZSM-5 Zeolites

Figures 2A, 2B:
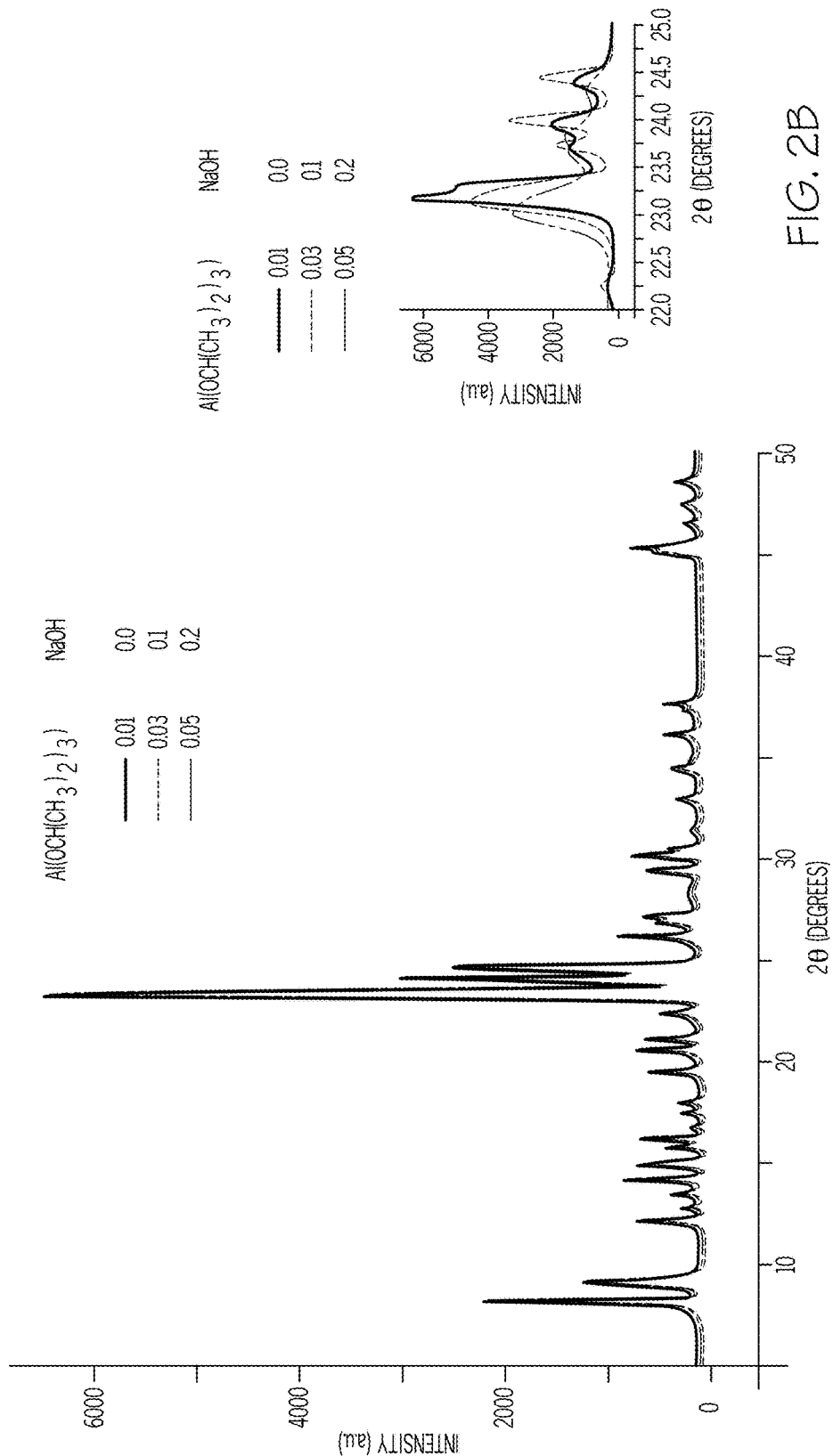
FIG. 2A is an X-ray Diffraction (XRD) pattern of the nano-ZSM-5 based catalyst embodiments at various of sodium hydroxide.
FIG. 2B is an enlarged segment of the XRD pattern of FIG. 2A.

The synthesized MFI-type zeolites with organic and organic-inorganic structure directing agents were examined by X-ray Diffraction (XRD) technique and the acquired data revealed an exact match with the diffraction pattern of MFI type zeolite structure as shown in FIGS. 2A and 2B.

Figure 3:
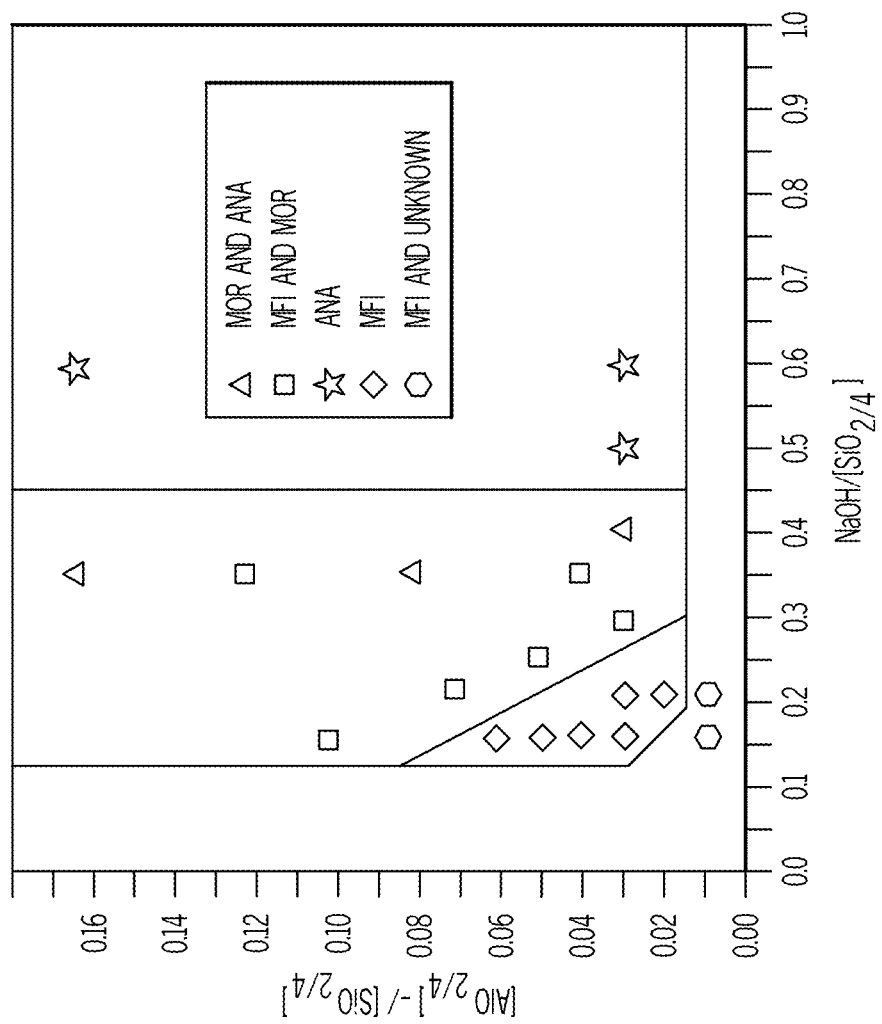
FIG. 3 is a graphical illustration of the phase selectivity of catalyst synthesis solutions based on the Al/Si and Na/Si ratios in the synthesis solution.

Moreover, the XRD was also used to develop a phase envelope where $[AlO_2/4]/[SiO_2/4]$ was plotted along the ordinate while $NaOH/[SiO_2/4]$ was plotted along the abscissa as presented in FIG. 3. The diagram determined that the MFI-type zeolite is only formed in a small region in the phase space. Solutions with relatively low concentrations of the sodium hydroxide (i.e., Si/Na ~5) and aluminum (i.e., Si/Al ~25) were found to lead to pure MFI-type products. Lower concentrations of the sodium hydroxide and alumina were observed to give some mixed phase products that included unknowns and relatively important concentrations of amorphous phases as shown in FIG. 3.

Figure 4A:
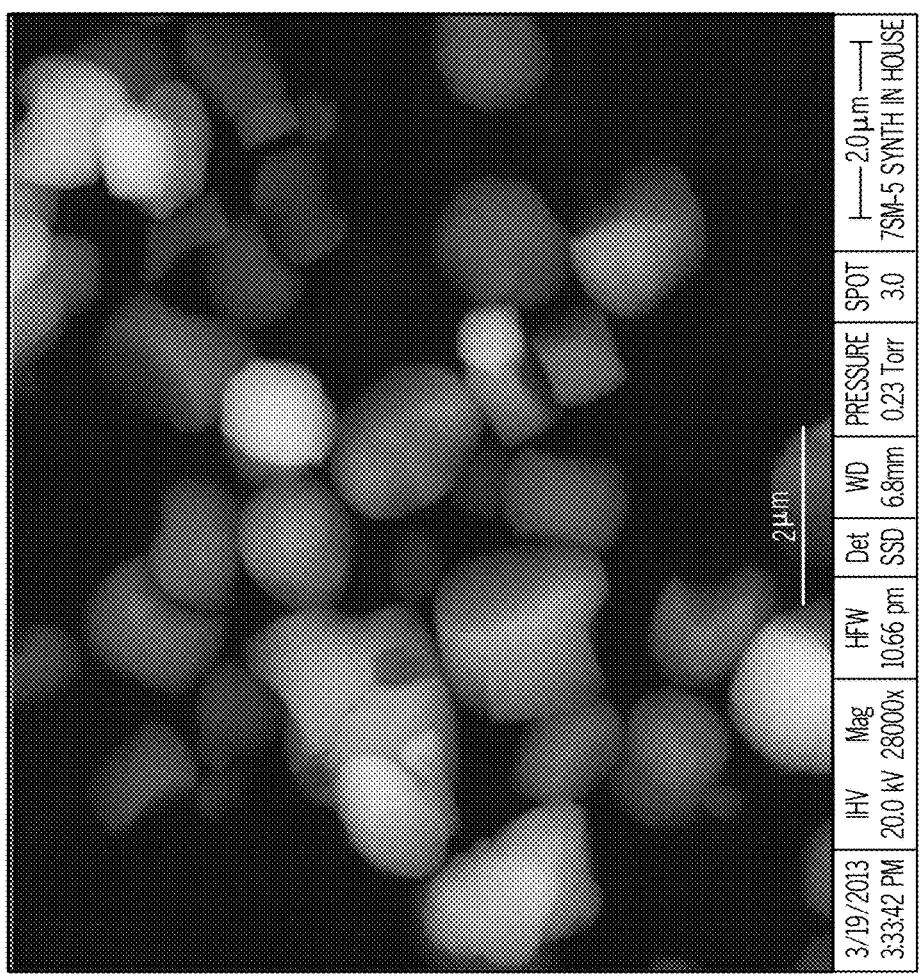
FIG. 4A is an environmental scanning electron microscopy (ESEM) micrograph of micron-size ZSM-5 zeolite embodiments.
Figure 4B:
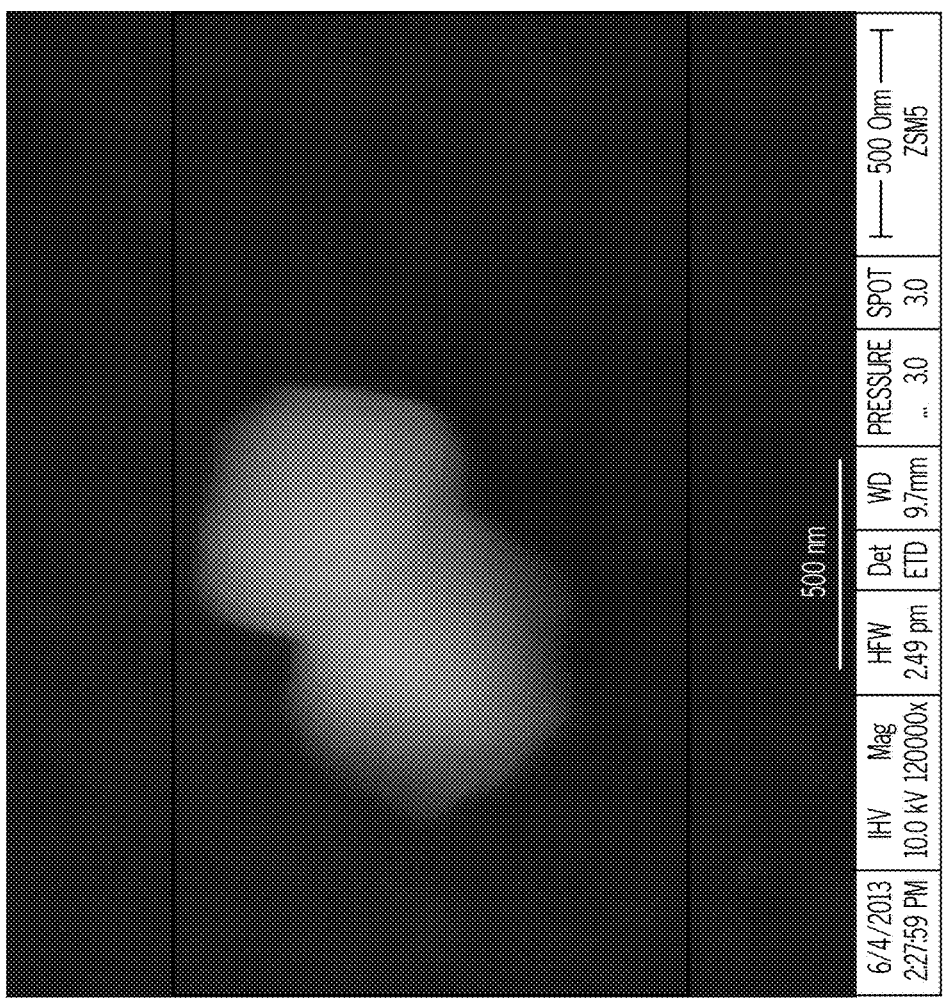
FIG. 4B is an ESEM micrograph of nano-ZSM-5 zeolite embodiments.

The obtained ESEM micrographs in FIGS. 4A and 4B were used to measure the particle size and to determine the surface morphologies of the synthesized samples. Selected samples were analyzed to indicate whether the produced MFI zeolites were nano-sized particles or micro-sized particles as shown in FIGS. 4A and 4B. The average particles size measurements for the selected samples are listed in Table 8.

TABLE 8

BET measurement of ZSM-5 zeolite.

| Sample | Zeolite | Size Characteristic | Surface Area ($cm^2/g$) | Particle Diameter (μm) |
|---|---|---|---|---|
| SAZ-11 | MFI | Micronsized Particles | 3 | 1.1 |
| SAZ-21 | MFI | Nanoparticles | 40 | 0.084 |
| SAZ-24 | MFI | Nanoparticles | 40 | 0.084 |
| SAZ-28 | MFI | Nanoparticles | 48 | 0.07 |

The thermogravimetric (TGA) analysis of any newly synthesized zeolites is an important characterization as the catalysts have to withstand a temperature range of 500-750° C. typical for the HSFCC process. The water and tetrapropylammonium (TPA+) content of the synthesized zeolites were calculated from the weight loss upon heating. The weight loss between 25-200° C. was attributed to water content desorbing from the zeolite. It was observed that the water desorbed between 25-200° C. was proportional to sodium content in the zeolite. In contrast, the more TPA+ in the sample, the less water desorbed from the sample in the heating process. This is due to the fact that the TPA+ is relatively large as compared to sodium ions. The TPA+ has hydrophobic properties that prevent the water molecules from adsorbing inside the zeolite samples. Moreover, the TPA+ fills the majority of the microspores leaving no space for water to attach to the zeolites (See Table 9).

Figure 5A:
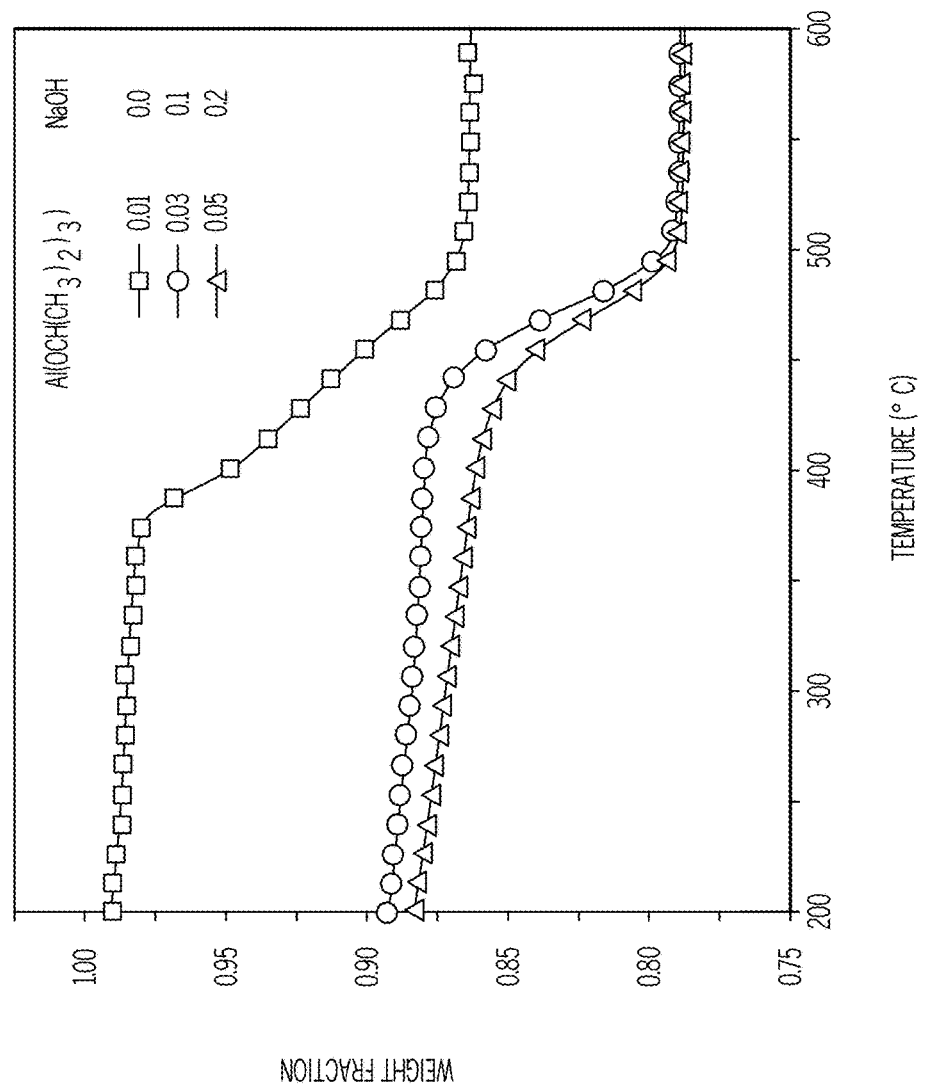
FIG. 5A is a graphical plot of Weight Fraction vs. Temperature which depicts the results of thermogravimetric analysis (TGA) conducted on ZSM-5 zeolite embodiments synthesized with different Na and Al concentrations.
Figure 5B:
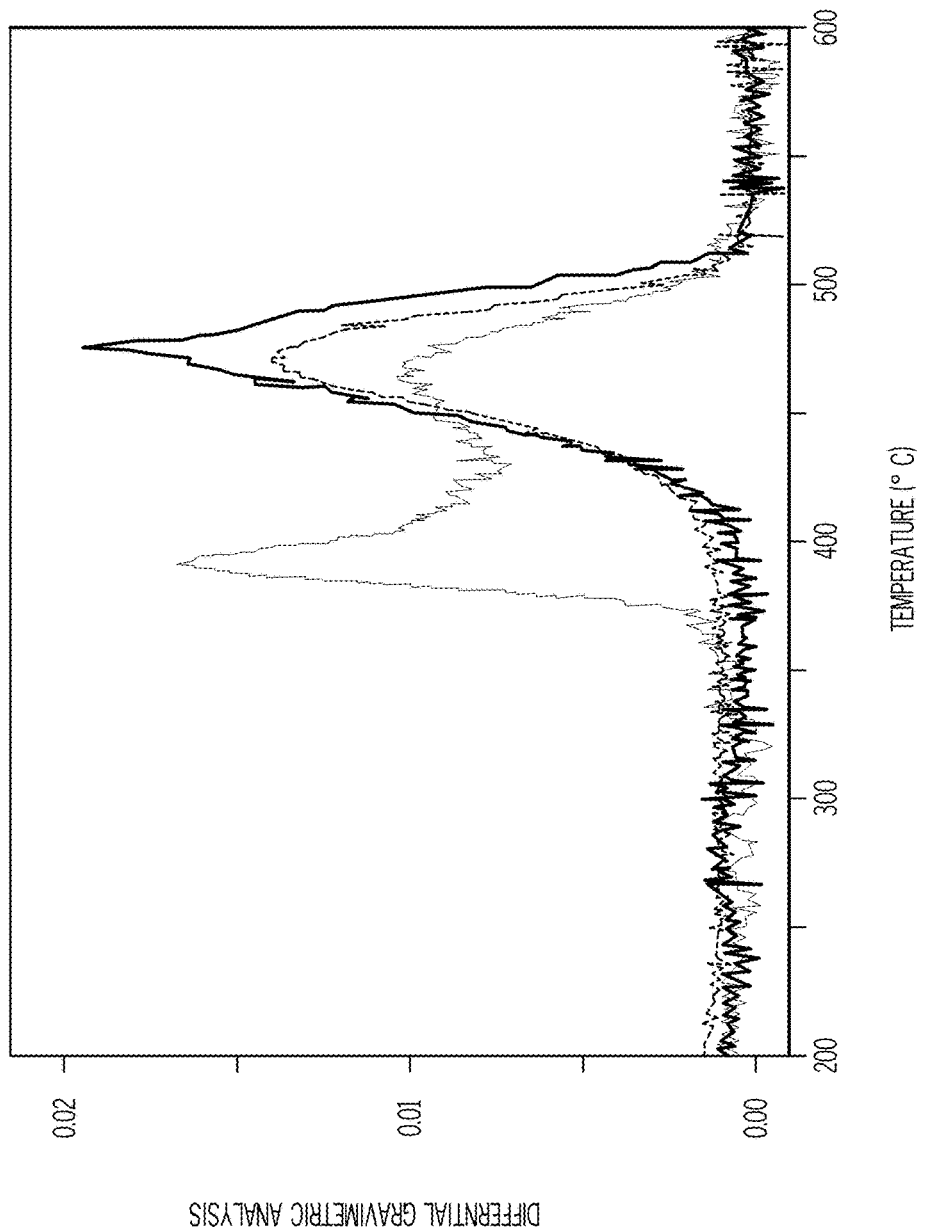
FIG. 5B is a graphical plot of Differential Gravimetric Analysis vs. Temperature which depicts further results of the TGA analysis of FIG. 5A conducted on ZSM-5 zeolite embodiments synthesized with different Na and Al concentrations.

At higher temperatures, between 200-550° C., the TPA+ converts to tripropylammonia and releases a propylene molecule. This gives rise to the weight loss, which is presented in FIGS. 5A and 5B. From TGA traces, the number of TPA atoms per unit cell can be calculated assuming no defect in the unit cell structure. An ideal MFI-type zeolite that is defect-free has the following molecular formula $(|TPAn|[Al_nSi_{96}\text{-}nO_{182}])$. Therefore, the number of TPA+ can be calculated using weight loss fraction and the molecular formula of MFI-type type zeolite as shown in Table 9.

TABLE 9

TGA analysis of ZSM-5 zeolites synthesized with different Na and Al concentrations.

| Sample content | | Weight fraction Loss | Weight Loss Between | Total Wight | Number of TPA$^+$ |
|---|---|---|---|---|---|
| Al | Na | Between 0 and 200° C. | 200 and 550° C. | loss | Molecules Per 96 $TO_2$ |
| 0.01 | 0 | 0.01 | 0.126 | 0.142 | 4.45 |
| 0.03 | 0.1 | 0.1074 | 0.1029 | 0.2129 | 3.54 |
| 0.05 | 0.2 | 0.1163 | 0.0952 | 0.2148 | 3.255 |

Figure 6A:
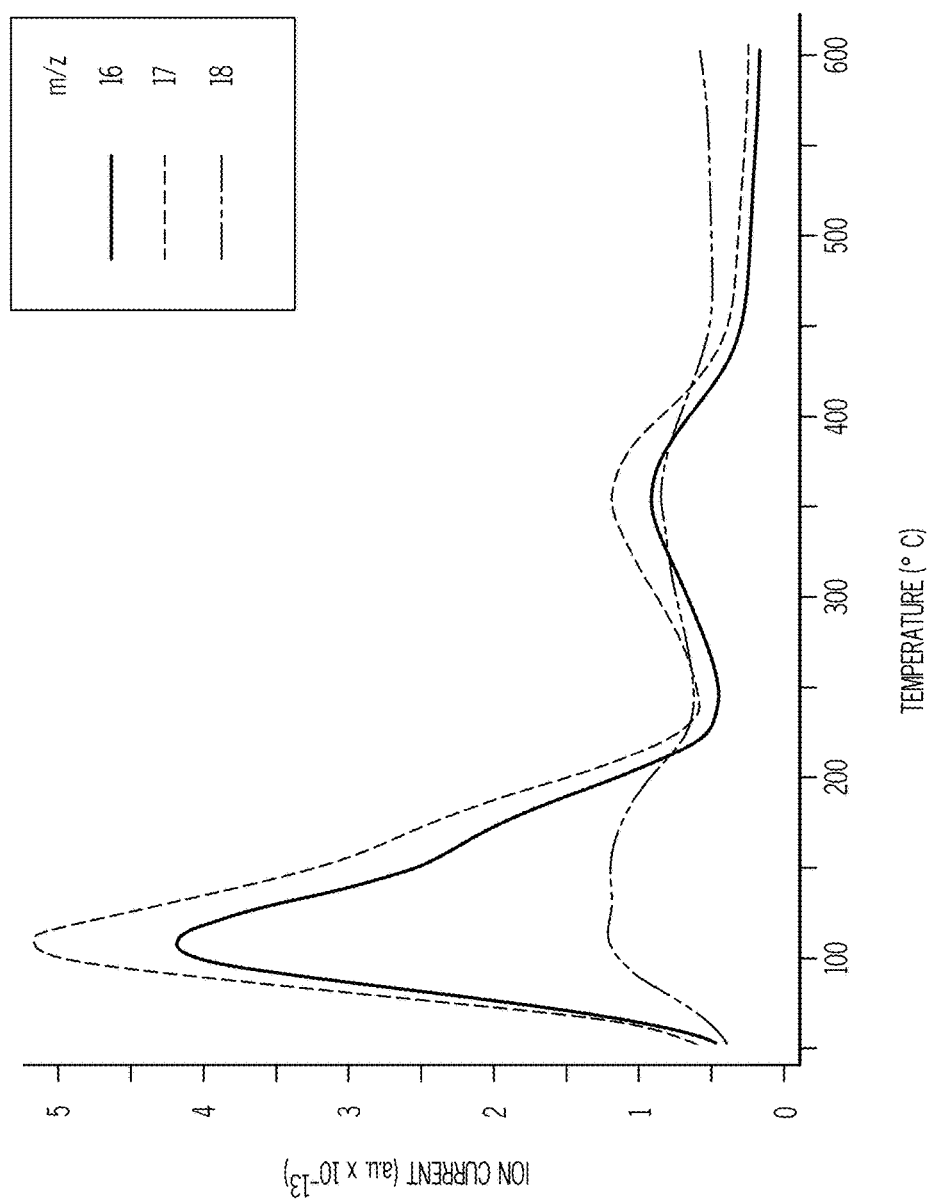
FIG. 6A is a Thermal Desorption Spectroscopy (TPD) curve depicting a high silica MFI-type zeolite embodiments prepared at Si/Al=100 at multiple mass to charge (m/z) ratios.
Figure 6B:
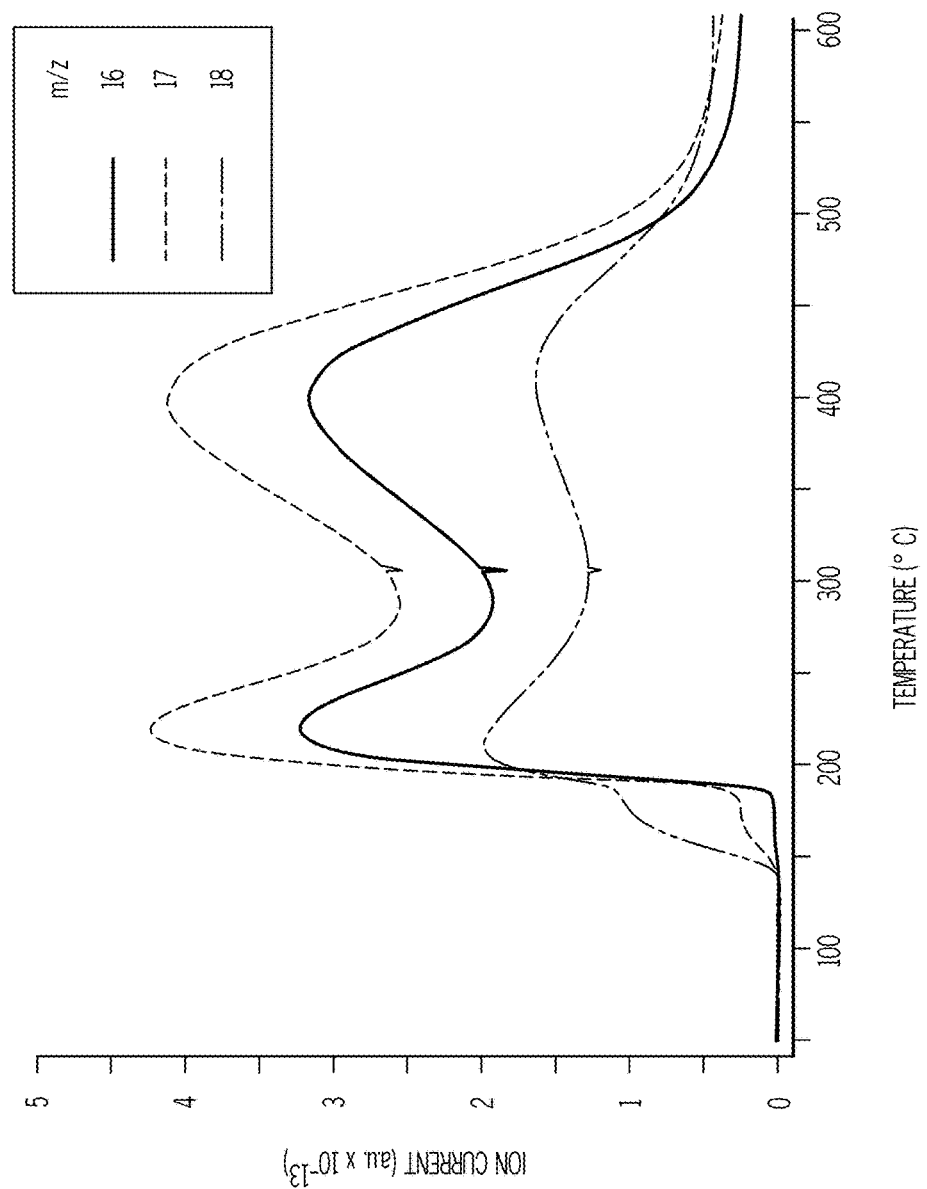
FIG. 6B is a TPD curve depicting a low silica MFI-type zeolite embodiments prepared at Si/Al=20 at multiple m/z ratios.

Referring to FIGS. 6A and 6B, temperature programmed desorption curves of high silicate sample and low silicate sample (high alumina) were collected. The mass to charge curves of 16, 17, and 18 corresponds to $NH_2+$, $NH_3+$, $H_2O+$ ions, respectively. The high silica sample exhibited two peaks with different energies. The low energy peak occurred at 109° C. and was attributed to weakly bonded ammonia. This low energy (low temperature) peak suggests the presence of silanol groups to which the ammonia was physisorbed. The peak at 350° C. was a high energy peak which represented strongly bonded ammonia into the strong Brønsted acid sites. A signal was observed between 200-500° C. that was split into two peaks at 225° C. and 400° C. for the high alumina samples. These peaks were higher in energy than the peaks detected for the high silica sample. They were assigned to Brønsted active sites present in the catalyst, which may give better cracking as more active sites are present. In conclusion, the presence of more alumina in the sample gave rise to peaks at higher temperature which were assigned to more Brønsted acid sites and less silanol groups bound to ammonia.

Characterization of Y Zeolites

Figure 7A:
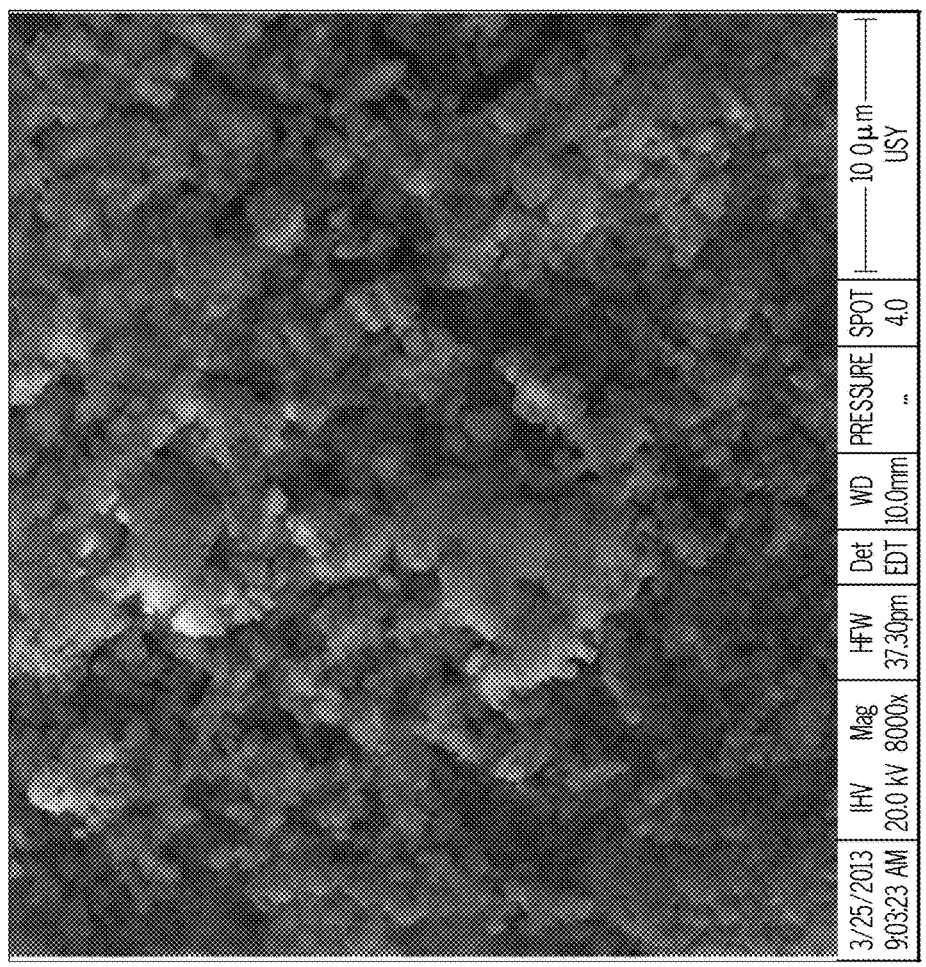
FIG. 7A is an ESEM image of a Y zeolite embodiment.
Figure 7B:
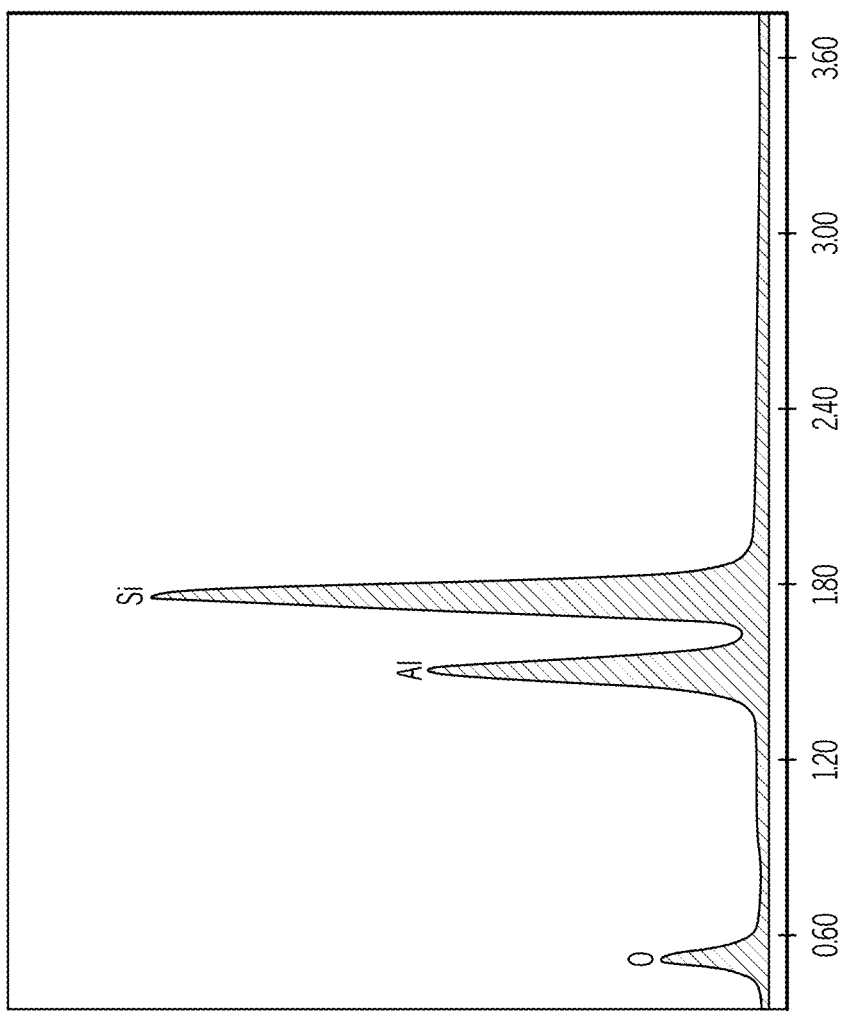
FIG. 7B is Energy Dispersive Spectrum (EDS) of the Y zeolite embodiment which corresponds to the ESEM of FIG. 7A.
Figure 8A:
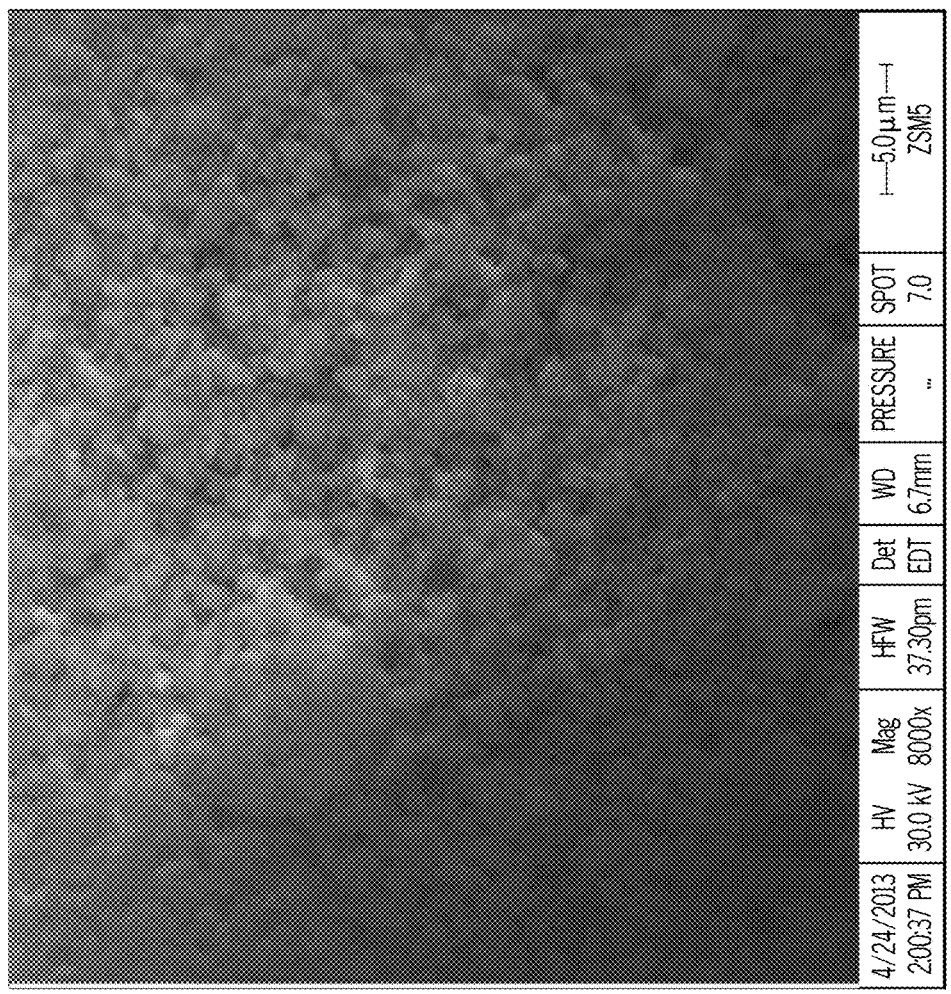
FIG. 8A is an ESEM image of a lanthanum-impregnated Y zeolite embodiment.
Figure 8B:
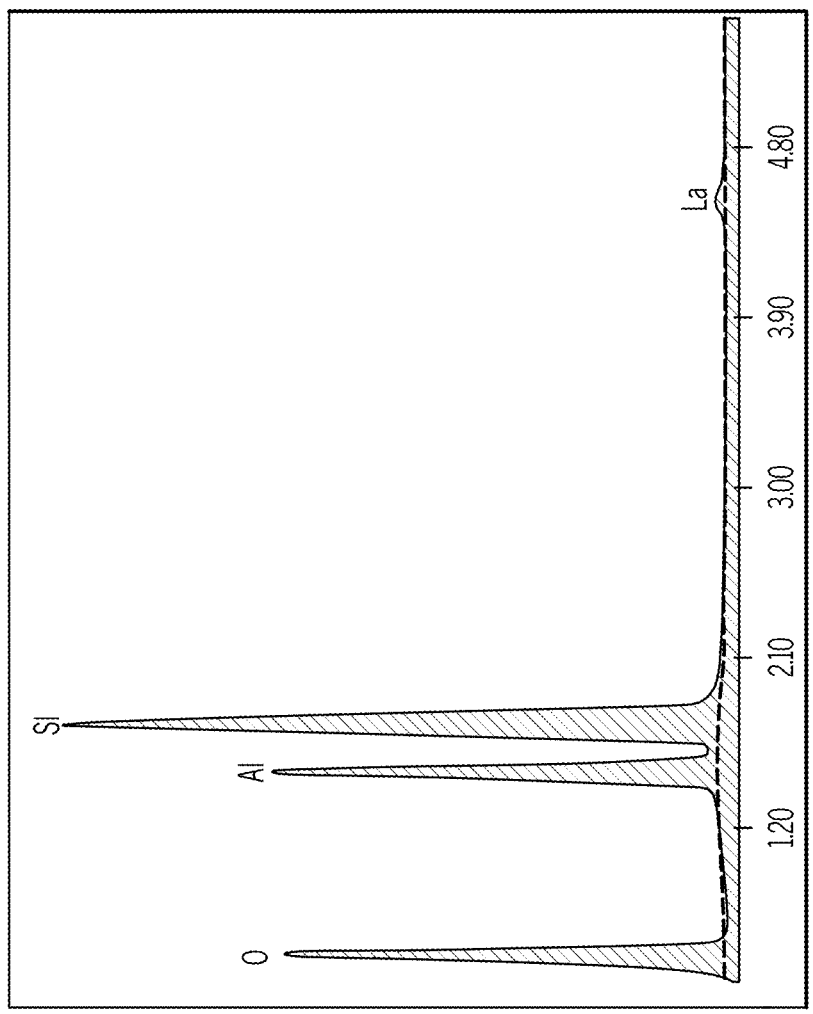
FIG. 8B is an EDS of the lanthanum-impregnated Y zeolite embodiment which corresponds to the ESEM of FIG. 8A.

As stated previously, USY zeolite impregnation with lanthanum impacts the selectivity towards light olefins. That being said, the ESEM analysis of both parent and impregnated Y zeolites, shown in FIGS. 7A and 8A, respectively, revealed no changes in the topographical features of the parent zeolites. On the other hand, the elemental analysis using EDS detector integrated within the ESEM indicated that the zeolite samples were mainly composed of silicon, aluminum, and oxygen in addition to lanthanum for the impregnated Y zeolite shown in FIG. 8B.

Figure 9:
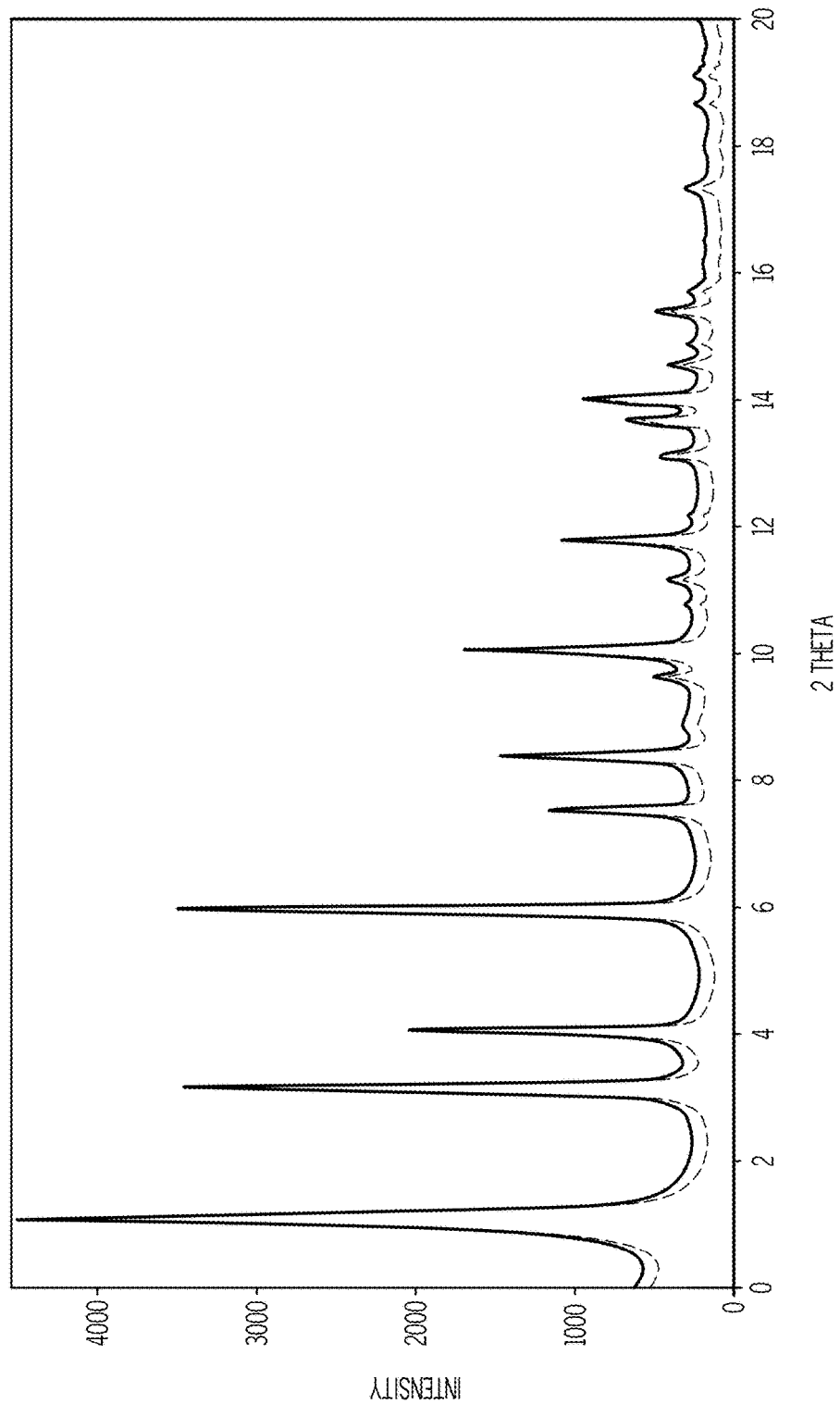
FIG. 9 is an XRD pattern of a parent Y zeolite embodiment versus its lanthanum impregnated Y zeolite form.

As shown in FIG. 9, an XRD analysis was used to investigate the effects of lanthanum impregnation on the crystallography structure of the parent Y zeolite. The produced diffractograms of both parent and impregnated forms of zeolites were identical, thus indicating no effect on crystal structure as shown in FIG. 9. Moreover, the surface area and pore volume analysis (See Table 10) revealed there was negligible difference between the Y zeolite and its impregnated form.

TABLE 10

BET measurements of Y zeolite.

| | Surface area | Pore volume |
|---|---|---|
| Y zeolite | 774 | 0.486 |
| La-impregnated Y zeolite | 774 | 0.482 |

It should be apparent to those skilled in the art that various modifications and variations can be made to the described embodiments without departing from the spirit and scope of the claimed subject matter. Thus it is intended that the specification cover the modifications and variations of the various described embodiments provided such modification and variations come within the scope of the appended claims and their equivalents.

The invention claimed is:

1. A method of converting gas condensate into a product stream comprising propylene, the method comprising:
    feeding gas condensate at a top region of a downflow high severity fluidized catalytic cracking reactor (HSFCC), the gas condensate comprising at least 50% by weight paraffins;
    feeding catalyst to the top region of the downflow HSFCC reactor in an amount characterized by a catalyst to gas condensate weight ratio of about 5:1 to about 40:1, where the catalyst comprises nano ZSM-5 zeolite catalyst having a Si/Al molar ratio from 20 to 40; and
    cracking the gas condensate in the presence of the catalyst at a reaction temperature of about 500° C. to about 700° C. to produce the product stream comprising propylene.

2. The method of claim 1 further comprising adding steam to the top region of the downflow HSFCC reactor.

3. The method of claim 1, where the cracking occurs at a pressure of about 1 to 2 atm to produce the product stream comprising propylene.

4. The method of claim 1, where the gas condensate comprises less than 0.1% by weight olefins.

5. The method of claim 1, where the Si/Al atomic ratio is from 25 to 35.

6. The method of claim 1, where the product stream comprises at least a 20 wt % yield of propylene.

7. The method of claim 1, where the product stream comprises at least a 10 wt % yield of ethylene.

8. The method of claim 1, where the nano ZSM-5 catalyst is impregnated with phosphorus.

9. The method of claim 1, where the catalyst comprises 10 to 50 wt % of nano ZSM-5 catalyst.

10. The method of claim 1, where the catalyst comprises USY (Ultrastable Y zeolite).

11. The method of claim 10, where the USY catalyst is impregnated with lanthanum.

12. The method of claim 10, where the catalyst comprises 10 to 50 wt % of USY catalyst.

13. The method of claim 1, where the catalyst comprises one or more of alumina, clay, and silica.

14. The method of claim 13, where the clay comprises one or more components selected from kaolin, montmorilonite, halloysite, and bentonite.

15. The method of claim 13, where the catalyst comprises 30 to 70 wt % of clay.

16. The method of claim 13, where the catalyst comprises 2 to 20 wt % of alumina.

17. The method of claim 13, where the catalyst comprises 0.1 to 10 wt % of silica.

18. The method of claim 1, where the reaction temperature is about 550° C. to about 630° C.

19. The method of claim 1, where the gas condensate has a residence time in the downflow fluidized catalytic cracking reactor of 0.7 seconds to 10 seconds.

20. The method of claim 1, where the catalyst to gas condensate ratio is 5:1 to about 10:1.

21. The method of claim 1, where the catalyst comprises the nano ZSM-5 catalyst, USY catalyst, alumina, clay, and silica.

22. The method of claim 1, where the catalyst comprises from 10 to 50 wt % of nano ZSM-5 catalyst, 10 to 50 wt % of USY catalyst, 2 to 20 wt % of alumina, 30 to 70 wt % of clay, and 0.1 to 10 wt % of silica.

23. The method of claim 1, where the gas condensate comprises naphthenes and aromatics.

24. The method of claim 23, where the gas condensate comprises 65 wt % paraffins, 0 wt % olefins, 21 wt % naphthenes, and 15 wt % aromatics.

25. The method of claim 1, where the gas condensate has an initial boiling point of at least 0° C. and a final boiling point of at least 450° C. when measured according to a true boiling point analysis.

26. The method of claim 1, where the nano ZSM-5 zeolites has a surface area of at least 30 cm$^2$/g.

27. The method of claim 1, where the gas condensate has a research octane number (RON) of 70 to 75 according to ASTM 2699 or ASTM 2700.

28. The method of claim 1, where the nano ZSM-5 zeolite catalyst has an average particle diameter from 0.01 to 0.2 µm.

29. The method of claim 1, where the nano ZSM-5 zeolite catalyst has a surface area of at least 20 cm$^2$/g.

* * * * *